United States Patent [19]

Estell et al.

[11] Patent Number: 5,182,204
[45] Date of Patent: Jan. 26, 1993

[54] NON-HUMAN CARBONYL HYDROLASE MUTANTS, VECTORS ENCODING SAME AND HOSTS TRANSFORMED WITH SAID VECTORS

[75] Inventors: David A. Estell, Mountain View; Richard R. Bott, Burlingame; Scott D. Power, San Bruno; James A. Wells, San Mateo, all of Calif.

[73] Assignee: Genencor International, Inc.
[21] Appl. No.: 807,786
[22] Filed: Dec. 11, 1991

Related U.S. Application Data

[63] Continuation of Ser. No. 84,589, Aug. 12, 1987, abandoned, and a continuation-in-part of Ser. No. 94,057, Sep. 3, 1987, abandoned, which is a continuation of Ser. No. 614,617, May 29, 1984, abandoned, and a continuation-in-part of Ser. No. 91,614, Aug. 31, 1987, abandoned, which is a continuation of Ser. No. 614,612, May 29, 1984, Pat. No. 4,760,025, and a continuation-in-part of Ser. No. 41,885, Apr. 22, 1987, abandoned, which is a continuation-in-part of Ser. No. 614,615, May 29, 1984, abandoned, and Ser. No. 35,652, Apr. 6, 1987, abandoned, which is a continuation-in-part of Ser. No. 858,594, Apr. 30, 1986, abandoned, which is a continuation-in-part of Ser. No. 614,612, May 29, 1984, Pat. No. 4,760,025, and Ser. No. 614,617, May 29, 1984, abandoned, and Ser. No. 614,615, May 29, 1984, abandoned, and Ser. No. 614,491, May 29, 1984, abandoned, and Ser. No. 858,594, Apr. 30, 1986, abandoned, which is a continuation-in-part of Ser. No. 614,612, May 29, 1984, Pat. No. 4,760,025, and Ser. No. 614,617, May 29, 1984, abandoned, and Ser. No. 614,615, May 29, 1984, abandoned, and Ser. No. 614,491, May 29, 1984, abandoned, and Ser. No. 924,162, Oct. 29, 1986, abandoned, which is a continuation-in-part of Ser. No. 614,491, May 29, 1984, abandoned, and Ser. No. 614,612, May 29, 1984, Pat. No. 4,760,025, and Ser. No. 614,617, May 29, 1984, abandoned, and Ser. No. 614,615, May 29, 1984, abandoned, and Ser. No. 614,491, May 29, 1984, abandoned.

[51] Int. Cl.$^5$ .................. C12N 9/56; C12N 9/54; C12N 1/21; C12N 15/55
[52] U.S. Cl. .................. 435/222; 435/221; 435/252.5; 435/320.1; 435/832; 435/91; 435/172.3; 435/172.1; 536/23.2; 930/240; 935/10; 935/14; 935/74
[58] Field of Search .............. 435/92, 221, 222, 252.5, 435/320.1, 832, 172.3; 536/27; 935/10, 14

[56] References Cited

U.S. PATENT DOCUMENTS 4,760,025 7/1988 Estell et al. ............... 435/222

OTHER PUBLICATIONS

Rastetter; W. H. 1983 Trends Biotechnol-1, 80–84.
Wells et al. 1987, Proc. Nat'l. Acad. Sci. USA, 84, 1219–1223.
Bryan et al. 1986 Proc. Nat'l. Acad. Sci. 83, 3743–3745.
Estell et al. 1986 Science 233, 659–663.

*Primary Examiner*—Robert A. Wax
*Assistant Examiner*—Christopher S. F. Low
*Attorney, Agent, or Firm*—Margaret A. Horn

[57] ABSTRACT

Novel carbonyl hydrolase mutants derived from the DNA sequences of naturally-occurring or recombinant non-human carbonyl hydrolases. The mutant carbonyl hydrolases, in general, are obtained by in vitro modification of a precursor DNA sequence encoding the naturally-occurring or recombinant carbonyl hydrolase to encode the substitution of an amino acid in the amino acid sequence of a precursor carbonyl hydrolase. Such mutants have properties which are different than the precursor hydrolase.

1 Claim, 2 Drawing Sheets

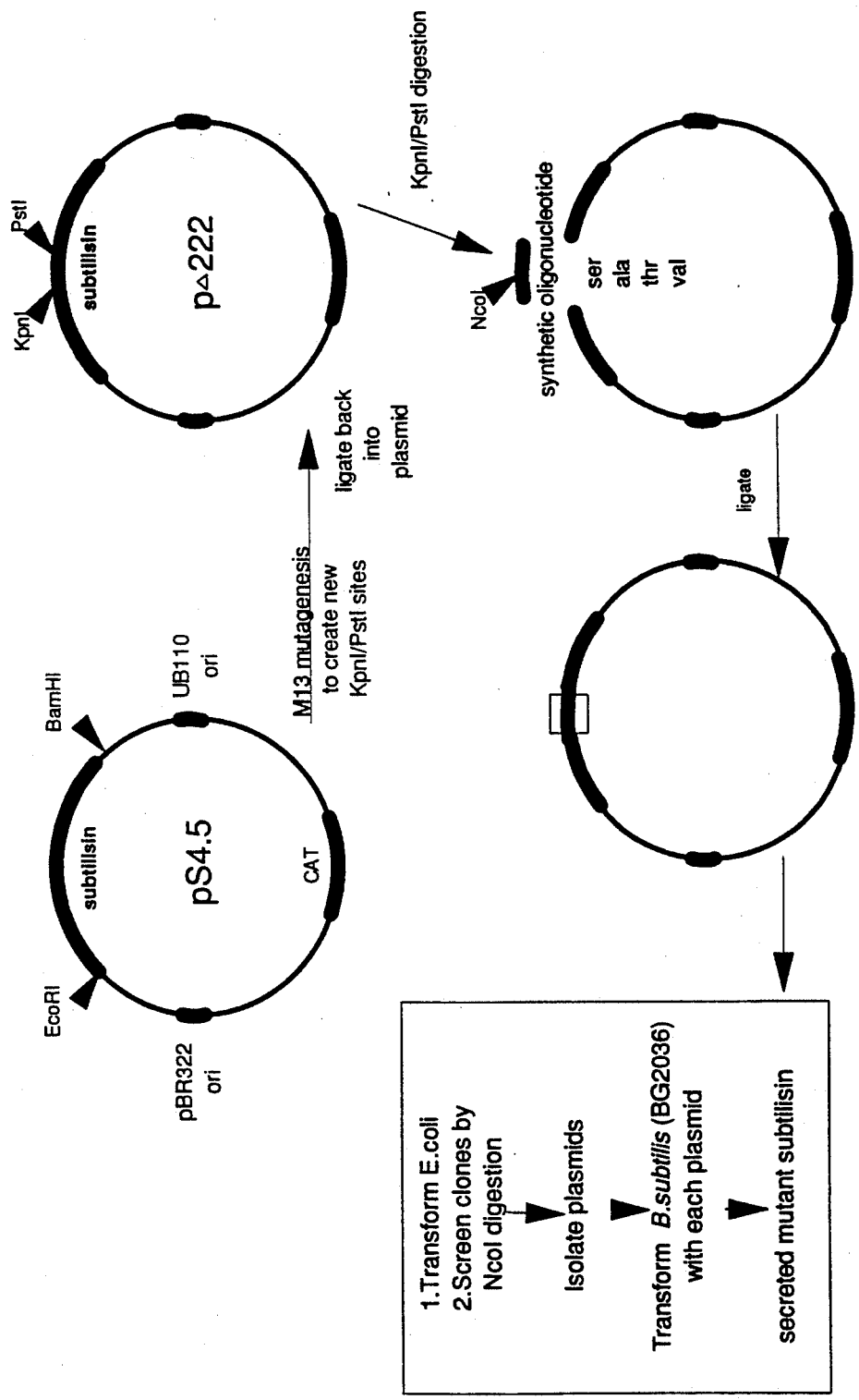
FIGURE 1 Cassette Mutagenesis method

FIGURE 2

Comparison of Subtilisins From *B.amyloliquifaciens* and *B.subtilis*

```
                        Hy1   Hy2
sub  1 .AQSVPYGISQIKAPALHSQGYTGSNVKVAIDSGIDSSHPDLNVRGGASF  50
amy  1  AQSVPYGVSQIKAPALHSQGYTGSNVKVAVIDSGIDSSHPDLKVAGGASM  50
                                  Hy3
 51 VPSETNPYQDGSSHGTHVAGTIAALNNSIGVLGVSPSASLYAVKVLDSTG 100
 51 VPSETNPFQDNNSHGTHVAGTVAALNNSIGVLGVAPSASLYAVKVLGADG 100
     Hy4                            Hy5
101 SGQYSWIINGIEWAISNNMDVINMSLGGPTGSTALKTVVDKAVSSGIVVA 150
101 SGQYSWIINGIEWAIANNMDVINMSLGGPSGSAALKAAVDKAVASGVVVV 150

151 AAAGNEGSSGSTSTVGYPAKYPSTIAVGAVNSSNQRASFSSAGSELDVMA 200
151 AAAGNEGTSGSSSTVGYPGKYPSVIAVGAVDSSNQRASFSSVGPELDVMA 200
     Hy6                    Hy7Hy8
201 PGVSIQSTLPGGTYGAYNGTSMATPHVAGAAALILSKHPTWTNAQVRDRL 250
201 PGVSIQSTLPGNKYGAYNGTSMASPHVAGAAALILSKHPNWTNTQVRSSL 250

251 ESTATYLGNSFYYGKGLINVQAAAQ 275
251 ENTTTKLGDSFYYGKGLINVQAAAQ 275
```

NON-HUMAN CARBONYL HYDROLASE MUTANTS, VECTORS ENCODING SAME AND HOSTS TRANSFORMED WITH SAID VECTORS

This application is a continuation of application Ser. No. 07/084,589 filed Aug. 12, 1987 (abandoned) and a continuation-in-part of application Ser. No. 07/094,057 filed Sep. 3, 1987 (abandoned) which is a continuation of application Ser. No. 06/614,617 filed May 29, 1984 (abandoned) and a continuation-in-part of application Ser. No. 07/091,614 filed Aug. 31, 1987 (abandoned) which is a continuation of application Ser. No. 06/614,612 filed May 29, 1984 which is now U.S. Pat. No. 4,760,025 and a continuation-in-part of application Ser. No. 07/041,885 filed Apr. 22, 1987 (abandoned) which is a continuation-in-part of application Ser. No. 06/614,615 filed May 29, 1984 (abandoned) and a continuation-in-part of application Ser. No. 07/035,652 filed Apr. 6, 1987 (abandoned) which is a continuation-in-part of application Ser. No. 06/858,594 filed Apr. 30, 1986 (abandoned) which is a continuation-in-part of application Ser. No. 06/614,612 filed May 29, 1984 which is now U.S. Pat. No. 4,760,025 and which is a continuation-in-part of application Ser. No. 06/614,617 filed May 29, 1984 (abandoned) and which is a continuation-in-part of application Ser. No. 06/614,615 filed May 29, 1984 (abandoned) and which is a continuation-in-part of application Ser. No. 06/614,491 filed May 29, 1984 (abandoned) and a continuation-in-part of application Ser. No. 06/858,594 filed Apr. 30, 1986 (abandoned) which is a continuation-in-part of application Ser. No. 06/614,612 filed May 29, 1984 which is now U.S. Pat. No. 4,760,025 and which is a continuation-in-part of application Ser. No. 06/614,617 filed May 29, 1984 (abandoned) and which is a continuation-in-part of application Ser. No. 06/614,615 filed May 29, 1984 (abandoned) and which is a continuation-in-part of application Ser. No. 06/614,491 filed May 29, 1984 (abandoned) and a continuation-in-part of application Ser. No. 06/924,162 filed Oct. 29, 1986 (abandoned) which is a continuation of application Ser. No. 06/614,491 filed May 29, 1984 (abandoned) and a continuation-in-part of application Ser. No. 06/614,612 filed May 29, 1984 which is now U.S. Pat. No. 4,760,025 and a continuation-in-part of application Ser. No. 06/614,617 filed May 29, 1984 (abandoned) and which is a continuation-in-part of application Ser. No. 06/614,615 filed May 29, 1984 (abandoned) and which is a continuation-in-part of application Ser. No. 06/614,491 filed May 29, 1984 (abandoned) each of which are incorporated herein by reference.

FIELD OF THE INVENTION

The present invention relates to novel carbonyl hydrolase mutants derived from the amino acid sequence of naturally-occurring or recombinant non-human carbonyl hydrolases and to DNA sequences encoding the same. Such mutant carbonyl hydrolases, in general, are obtained by in vitro modification of a precursor DNA sequence encoding the naturally-occurring or recombinant carbonyl hydrolase to encode the substitution, insertion or deletion of one or more amino acids in a precursor amino acid sequence.

BACKGROUND OF THE INVENTION

Serine proteases are a subgroup of carbonyl hydrolase. They comprise a diverse class of enzymes having a wide range of specificities and biological functions. Stroud, R. M. (1974) Sci Amer. 131, 74–88. Despite their function diversity, the catalytic machinery of serine proteases has been approached by at least two genetically distinct families of enzymes: the Bacillus subtilisins and the mammalian and homologous bacterial serine proteases (e.g., trypsin and S. gresius trypsin). These two families of serine proteases show remarkably similar mechanisms of catalysis. Kraut, J. (1977) Ann. Rev. Biochem. 46, 331–358. Furthermore, although the primary structure is unrelated, the tertiary structure of these two enzyme families bring together a conserved catalytic triad of amino acids consisting of serine, histidine and aspartate.

Subtilisin is a serine endoprotease (MW 27,500) which is secreted in large amounts from a wide variety of Bacillus species. The protein sequence of subtilisin has been determined from at least four different species of Bacillus. Markland, F. S., et al. (1971) in *The Enzymes*, ed. Boyer P. D., Acad Press, New York, vol. III, pp. 561–608; Nedkov, P. et al. (1983) *Hoppe-Seyler's Z. Physiol. Chem.* 364, 1537–1540. The three-dimensional crystallographic structure of subtilisin BPN' (from *B. amyloligoefaciens*) to 2.5 A resolution has also been reported. Wright, C. S., et al. (1969) *Nature* 221, 235–242; Drenth, J. et al. (1972) *Eur. J. Biochem.* 26, 177–181. These studies indicate that although subtilisin is genetically unrelated to the mammalian serine proteases, it has a similar active site structure. The x-ray crystal structures of subtilisin containing covalently bound peptide inhibitors (Robertus, J. D., et al. (1972) *Biochemistry* 11, 2439–2449), product complexes (Robertus, J. D., et al. (1972) *Biochemistry* 11, 4293–4303), and transition state analogs (Matthews, D. A., et al. (1975) *J. Biol. Chem.* 250, 7120–7126; Poulos, T. L., et al. (1976) *J. Biol. Chem.* 251, 1097–1103), which have been reported have also provided information regarding the active site and putative substrate binding cleft of subtilisin. In addition, a large number of kinetic and chemical modification studies have been reported for subtilisin (Philipp, M., et al. (1983) *Mol. Cell. Biochem.* 51, 5–32; Svendsen, I. B. (1976) *Carlsberg Res. Comm.*, 41, 237–291; Markland, F. S. Id.) as well as at least one report wherein the side chain of methione at residue 222 of subtilisin was converted by hydrogen peroxide to methionine-sulfoxide (Stauffer, D. C., et al. (1965) *J. Biol. Chem.* 244, 5333–5338).

Substrate specificity is a ubiquitous feature of biological macromolecules that is determined by chemical forces including hydrogen bonding, electrostatic, hydrophobic and steric interactions. Jencks, W. P., in *Catalysis in Chemistry and Enzymology* (McGraw-Hill, 1969) pp. 321–436; Fersht. A., in *Enzyme Structure and Mechanism* (Freeman, San Francisco, 1977) pp. 226–287. Substrate specificity studies of enzymes, however, have been limited to the traditional means of probing the relative importance of these binding forces. Although substrate analogs can be synthesized chemically, the production of modified enzyme analogs has been limited to chemically modified enzyme derivatives (Kaiser, E. T., et al. (1985) *Ann. Rev. Biochem.* 54, 565–595 or naturally occurring mutants. Kraut, J. (1977) *Ann. Rev. Biochem.* 46, 331–358.

The recent development of various in vitro techniques to manipulate the DNA sequences encoding naturally-occuring polypeptides as well as recent developments in the chemical synthesis of relatively short sequences of single and double stranded DNA has resulted in the speculation that such techniques can be used to modify enzymes to improve some functional property in a predictable way. Ulmer, K. M. (1983) *Science* 219, 666-671. The only working example disclosed therein, however, is the substitution of a single amino acid within the active site of tyrosyl-tRNA synthetase (Cys35→Ser) which lead to a reduction in enzymatic activity. See Winter, G. et al. (1982) *Nature* 299, 756-758; and Wilkinson, A. J., et al. (1983) *Biochemistry* 22, 3581-3586 (Cys35-Gly mutation also resulted in decreased activity).

When the same t-RNA synthetase was modified by substituting a different amino acid residue within the active site with two different amino acids, one of the mutants (Thr51→Ala) reportedly demonstrated a predicted moderate increase in kcat/Km whereas a second mutant (Thr51→Pro) demonstrated a massive increase in kcat/Km which could not be explained with certainty. Wilkinson, A. H., et al. (1984) *Nature* 307, 187-188.

Another reported example of a single substitution of an amino acid residue is the substitution of cysteine for isoleucine at the third residue of T4 lysozyme. Perry, L. J., et al. (1984) *Science* 226, 555-557. The resultant mutant lysozyme was mildly oxidized to form a disulfide bond between the new cysteine residue at position 3 and the native cysteine at position 97. This crosslinked mutant was initially described by the author as being enzymatically identical to, but more thermally stable than, the wild type enzyme. However, in a "Note Added in Proof", the author indicated that the enhanced stability observed was probably due to a chemical modification of cysteine at residue 54 since the mutant lysozyme with a free thiol at Cys54 has a thermal stability identical to the wild type lysozyme.

Similarly, a modified dehydrofolate reductase from *E. coli* has been reported to be modified by similar methods to introduce a cysteine which could be crosslinked with a naturally-occurring cysteine in the reductase. Villafranca, D. E., et al. (1983) *Science* 222, 782-788. The author indicates that this mutant is fully reactive in the reduced state but has significantly diminished activity in the oxidized state. In addition, two other substitutions of specific amino acid residues are reported which resulted in mutants which had diminished or no activity.

As set forth below, several laboratories have also reported the use of site directed mutagensis to produce the mutation of more than one amino acid residue within a polypeptide.

The amino-terminal region of the signal peptide of the prolipoprotein of the *E. coli* outer membrane was stated to be altered by the substitution or deletion of residues 2 and 3 to produce a charge change in that region of the polypeptide. Inoyye, S., et al., (1982) *Proc. Nat. Acad. Sci. USA* 79, 3438-3441. The same laboratory also reported the substitution and deletion of amino acid redisues 9 and 14 to determine the effects of such substitution on the hydrophobic region of the same signal sequence. Inouye, S., et al., (1984) *J. Biol. Chem.* 259, 3729-3773. In the case of mutants at residues 2 and 3 the authors state that the results obtained were consistent with the proposed loop model for explaining the functions of the signal sequence. However, as reported the mutations at residues 9 and 14 produced results indicating that the signal peptide has unexpeded flexibility in terms of the relationship between its primary structure and function in protein secretion.

Double mutants in the active site of tyrosyl-t-RNA synthetase have also been reported. Carter, P. J., et al. (1984) *Cell* 38, 835-840. In this report, the improved affinity of the previously described Thr51→Pro mutant for ATP was probed by producing a second mutation in the active site of the enzyme. One of the double mutants, Gly35/Pro51, reportedly demonstrated an unexpected result in that it bound ATP in the transition state better than was expected from the two single mutants. Moreover, the author warns, at least for one double mutant, that it is not readily predictable how one substitution alters the effect caused by the other substitution and that care must be taken in interpreting such substitutions.

A mutant is disclosed in U.S. Pat. No. 4,532,207, wherein a polyarginine tail was attached to the C-terminal residue of β-urogastrone by modifying the DNA sequence encoding the polypeptide. As disclosed, the polyarginine tail changed the electrophoretic mobility of the urogastrone-polyaginine hybrid permiting selective purification. The polyarginine was subsequently removed, according to the patentee, by a polyarginine specific exopeptidase to produce the purified urogastrone. Properly construed, this reference discloses hybrid polypeptides which do not constitute mutant polypeptides containing the substitution, insertion or deletion of one or more amino acids of a naturally occurring polypeptide.

Single and double mutants of rat pancreatic trypsin have also been reported. Craik, C. S., et al. (1985) *Science* 228, 291-297. As reported, glycine residues at positions 216 and 226 were replaced with alanine residues to produce three trypsin mutants (two single mutants and one double mutant). In the case of the single mutants, the authors stated expectation was to observe a differential effect on Km. They instead reported a change in specificity (kcat/Km) which was primarily the result of a decrease in kcat. In contrast, the double mutant reportedly demonstrated a differential increase in Km for lysyl and arginyl substrates as compared to wild type trypsin but had virtually no catalytic activity.

The references discussed above are provided solely for their disclosure prior to the filing data of the instant case, and nothing herein is to be construed as an admission that the inventors are not entitled to antedate such disclosure by virtue of prior invention or priority base on earlier filed applications.

Based on the above references, however, it is apparent that the modification of the amino acid sequence of wild type enzymes often results in the decrease or destruction of biological activity. Moreover, these references do not address the mutation of the particular carbonyl hydrolases disclosed herein.

Accordingly, it is an object herein to provide carbonyl hydrolase mutants which have at least one property which is different from the same property of the carbonyl hydrolase precursor from which the amino acid of said mutant is derived.

It is a further object to provide mutant DNA sequences encoding such carbonyl hydrolase mutants as well as expression vectors containing such mutant DNA sequences.

Still further, another object of the present invention is to provide host cells transformed with such vectors as well as host cells which are capable of expressing such mutants either intracellularly or extracellularly.

SUMMARY OF THE INVENTION

The invention includes carbonyl hydrolase mutants having a different kcat/Km and subsequently a different substrate specificity from the precursor non-human carbonyl hydrolase from which the amino acid sequence of the mutant is derived. The precursor carbonyl hydrolase may be a naturally occurring carbonyl hydrolase or recombinant hydrolase. Specifically the mutants are carbonyl hydrolase mutants having an amino acid sequence not found in nature and which is derived by replacement of one amino acid residue or precursor subtilisin with a different amino acid. Said one amino acid residue is selected from the group consisting of amino acid residues of:

a) *Bacillus amyloliquefaciens* subtilisin ser 224;
b) *Bacillus subtilis* subtilisin thr 224; and
c) equivalent amino acid residues to said a) and b) residues in other precursor subtilisin.

It is understood that it is preferred that the resultant mutant will have the substitution which is different than the naturally occurring amino acid residue for that particular carbonyl hydrolase. So, for example, a mutant of the invention will have other than ser 224 in *Bacillus amyloliquefaciens* subtilisin or other than 224 in *Bacillus subtilis* subtilisin, but *Bacillus amyloliquefaciens* subtilisin may have thr 224 mutants or *Bacillus subtilis* subtilisin mutants may have ser 224 mutants.

The invention also includes mutant DNA sequences encoding such carbonyl hydrolase mutants. These mutant DNA sequences are derived form a precursor DNA sequence which encodes a naturally occurring or recombinant precursor carbonyl hydrolase. The mutant DNA sequence is derived by modifying the precursor DNA sequence to encode the substitution of one amino acid encoded by the precursor DNA sequence. These recombinant DNA sequences encode mutants having an amino acid sequence which does not exist in nature and at least one property which is substantially different from the same property of the precursor carbonyl hydrolase encoded by the precursor DNA sequence.

Further the invention includes expression vectors containing such mutant DNA sequences as well as host cells transformed with such vectors which are capable of expressing said carbonyl hydrolase mutants.

BRIEF DESCRIPTION OF THE DRAWINGS

FIG. 1 shows the Cassette Mutagenesis Method of the production of the carbonyl hydrolase mutants of the invention.

FIG. 2 shows a comparison of the amino acid sequences of *Bacillus amyloliquefaciens* subtilisin and *Bacillus subtilis* subtilisin.

DETAILED DESCRIPTION OF THE INVENTION

The inventors have discovered that in vitro mutations at position 224 or equivalent amino acid residues of non-human carbonyl hydrolases increase kcat/Km ratio and hence alter substrate specificity.

Non-human carbonyl hydrolases, recombinant carbonyl hydrolases, subtilisins, recombinant subtilisins, carbonyl hydrolase mutant, equivalent amino acid residues, prosequence, signal sequence, prepro, expression vector, host cells, operably linked, cassette mutagenesis, substrate specificity, multiple mutants and mutants at various other amino acid residues are described in detail in parent application, Ser. No. 035,652 filed Apr. 6, 1987, and such definitions are incorporated herein by reference.

A change in substrate specificity is defined as a difference between the kcat/Km ratio of the precursor carbonyl hydrolase and that of the hydrolase mutant. The kcat/Km ratio is a measure of catalytic efficiency. Carbonyl hydrolase mutants with increased or diminished kcat/Km ratios are described in the examples. Generally, the objective will be to secure a mutant having a greater (numerically large) kcat/Km ratio for a given substrate, thereby enabling the use of the enzyme to more efficiently act on a target substrate. A substantial change in kcat/Km ratio is preferably at least a 2-fold increase or decrease. However, smaller increases or decreases in the ratio (e.g., at least 1.5-fold) are also considered substantial. An increase in kcat/Km ratio for one substrate may be accompanied by a reduction in kcat/Km ratio for another substrate. This is a shift in substrate specificity, and mutants exhibiting such shifts have utility where the precursor hydrolase is undesirable, e.g. to prevent undesired hydrolysis of a particular substrate in an admixture of substrates. Km and kcat are measured in accord with known procedures, as described in EPO Publication No. 0130756 or as described herein.

Construction and characterization of position 224 mutations. To confirm the importance of residue 224 and to analyze its role in catalytic activity, cassette mutagenesis was carried out at the 224 position of *Bacillus amyloliquefaciens* subtilisin, as described in FIG. 1. Four pairs of synthetic oligonucleotides were used to mutate codon 224 to either serine, alanine, threonine, or valine. The position 224 serine mutation was included as a control, and also to introduce, by means of a silent mutation, as NcoI site into an otherwise wild type *Bacillus amyloliquefaciens* subtilisin gene. The 224 alanine mutation was made to examine the effect of substituting for serine an isosteric amino acid lacking the hydroxyl group and the threonine and valine mutations were made to examine the effects of substituting an amino acid identical to that found in subtilisin or one isosteric with it.

The procedure used to make these several mutations in the *Bacillus amyloliquefaciens* subtilisin gene is illustrated in FIG. 1. Two restriction sites, KpnI and PstI, flanking the sequence around codons 221 to 226 had previously been introduced into the *Bacillus amyloliquefaciens* subtilisin gene by site directed mutagenesis. In addition to the mutations generating the two restriction sites, plasmid PD222 has a 10 base pairs deletion removing codons 222, 223, 224 and part of 225 and is thus incapable of encoding a functional protein. The coding capacity of the plasmid can be restored by inserting an appropriate double stranded oligonucleotide or "cassette" carrying wild type or mutant codons. "Cassette mutagenesis", is a simple and highly efficient method of mutagenizing specific regions of genes. In two separate experiments, one involving insertion of the serine and threonine codons, the other involving insertion of the alanine or valine codons, an efficiency of mutation of 50% as determined by screening for introduction of the diagnostic NcoI site contained in the cassette was obtained. Quadruplicate clones from the first mutagenesis and duplicate clones from the second were used to transform *B. subtilis* and transformants were plated on Luria agar containing skim milk in order to detect protease secretion. Only one of 12 candidate clones failed to secrete detectable subtilisin. For each mutant, one protease secreting transformant was selected for enzyme purification and characterization and for sequence analysis to ensure that the coding sequences in and around the cassette were correct.

The results of Kinetic studies with mutant subtilisins are shown in Table 1 in comparison with the type enzyme (*Bacillus amyloliquefaciens*) or subtilisin from *B. subtilis*. A change in the position 224 residue from serine (present in wild type *Bacillus amyloliquefaciens* subtilisin) to threonine (the residue found in subtilisin from *B. subtilis*) or to valine resulted in a decrease in kcat of approximately 3 fold or 17 fold respectively and a slight increase in Km to about $3 \times 10^{-4}M$ from $1.3 \times 10^{-M}$ wild type *Bacillus amyloliquefaciens* subtilisin The corresponding decreases in kcat/Km were approximately 7 fold, and 45 fold for mutations to threonine or valine respectively. In contrast, changing residue 224 to alanine had negligible effect on the kinetic properties of subtilisin indicating that the hydroxyl groups of residues present at 224 in both the amyloliquefaciens and subtilisins enzymes were not important for catalytic activity and that changes in Km and kcat as a result of substitutions at this site likely resulted from steric effects.

To examine the effect that position 224 mutations has on substrate specificity and to further explore the possibility that reductions in kcat and kcat/Km in going from serine to threonine or valine at position 224 might be due to steric effects on substrate binding, the kinetics of hydrolysis of three additional substrates by wild type and mutant enzymes was analyzed. The results are shown in Table 2 where Km, kcat/Km and DDGe are tabulated, the latter parameter representing the change in free energy of binding to the transition state when one substrate is substituted for another. The fluctuations in DDGe resulting from mutations at the 224 position thus are a measure of the resultant changes in substrate specificity. It can be seen from Table 2 that the maximum effect on DDGe fluctuation occurs when the substrate is altered at the P1 position (compare AAPF with AAPM), that changes at the P2 position have little effect (AAPF vs AAAF), and that the effects of altering the P4 position of the substrate are negligeable (AAAF vs FAAF). Furthermore the effect of the 224 threonine substitution in *Bacillus amyloliquefaciens* subtilisin, and even more the mutation to valine, is to increase the preference of the resulting enzyme for substrates with less bulky residues at the P1 position. In other words kcat/Km for the V224 enzyme increases more than 3 fold when the P1 residue of the substrate is methionine rather than phenylalanine, whereas it decreases approximately 2.5-3 fold for the wild type or A224 enzymes.

Having described the preferred embodiments of the present invention, it will appear to those ordinarily skilled in the art that various modifications may be made to the disclosed embodiments, and that such modifications are intended to be within the scope of the present invention.

TABLE 1

| Kinetics of postion 224 mutant subtilisins. | | | |
|---|---|---|---|
| ENZYME | Relative S.A. | Km | kcat | kcat/Km |
| WT* | 100 | 1.26E−04 | 47.6 | 3.78E+05 |
| S224 | 89 | 1.32E−04 | 43.5 | 3.30E+05 |
| A224 | 94 | 1.33E−04 | 45.5 | 3.42E+05 |
| T224 | 21 | 3.03E−04 | 15.5 | 5.12E+04 |
| V224 | 4 | 3.29E−04 | 2.7 | 8.21E+03 |
| I168** | 12 | 3.25E−04 | 7.0 | 2.15E+04 |

*Bacillus amuloliquefaciens subtilisin
**Bacillus subtilis strain I168 subtilisin

TABLE 2

| Effect of position 224 mutations on substrate specificites | | | | | | | |
|---|---|---|---|---|---|---|---|
| | sucAAPFna | | | sucAAPMna | | | DDFe |
| ENZYME | Km | kcat | kcat/Km | Km | kcat | kcat/Km | (P1) |
| AMY* | 1.26E−4 | 47.6 | 3.78E+05 | 9.71E−5 | 14.5 | 1.49E+5 | −0.55 |
| S224 | 1.32E−4 | 43.5 | 3.30E+05 | 9.82E−5 | 13.0 | 1.33E+5 | −0.54 |
| A224 | 1.33E−4 | 45.5 | 3.42E+05 | 1.05E−4 | 12.7 | 1.20E+5 | −0.62 |
| T224 | 3.03E−4 | 15.5 | 5.10E+04 | 1.14E−4 | 8.1 | 7.13E+4 | 0.20 |
| V224 | 3.29E−4 | 2.7 | 8.21E+03 | 1.40E−4 | 3.9 | 2.83E+4 | 0.73 |
| SUB** | 3.25E−4 | 7.0 | 2.15E+04 | 1.98E−4 | 8.5 | 4.28E+4 | 0.41 |

| | sucAAAFna | | | | sucFAAFna | | |
|---|---|---|---|---|---|---|---|---|
| ENZYME | Km | kcat | kcat/Km | DDGe (P2) | Km | kcat | kcat/Km | DDGe (P4) |
| AMY* | 2.25E−6 | 9.3 | 4.12E+06 | 1.41 | 1.88E−6 | 7.6 | 4.04E+06 | −0.01 |
| S224 | 2.13E−6 | 8.3 | 3.90E+06 | 1.46 | 1.74E−6 | 6.9 | 3.97E+06 | 0.01 |
| A224 | 2.14E−6 | 7.9 | 3.69E+06 | 1.40 | 1.98E−6 | 6.3 | 3.18E+06 | −0.09 |
| T224 | 4.13E−6 | 3.4 | 8.23E+05 | 1.64 | 3.15E−6 | 2.1 | 6.67E+05 | −0.12 |
| V224 | 6.51E−6 | 1.3 | 2.06E+05 | 1.90 | 3.76E−6 | 0.6 | 1.57E+05 | −0.16 |
| SUB** | 4.74E−6 | 5.4 | 1.14E+06 | 2.34 | 2.93E−6 | 3.7 | 1.26E+06 | 0.06 |

*Bacillus amyloliquefaciens subtilisin
**Bacillus subtilis strain I168 subtilisin

What is claimed is:

1. An essentially pure subtilisin having a different amino acid than that naturally occurring in said subtilisin at the position equivalent to ser+224 in subtilisin naturally produced by *Bacillus amyloliquefaciens*, as shown in FIG. 2, where in different amino acid is one of the twenty naturally occurring L-amino acids wherein the Kcat/Km ratio of the resulting subtilisin is altered by at least 1.5 fold compared to a subtilisin wherein the amino acid residue in said subtilisin equivalent to ser+224 in *Bacillus amyloliquefaciens* is the same as that which is naturally occurring for said subtilisin and wherein the synthetic substrate is selected from the group consisting of AAPF, AAPM, AAAF or FAAF.

* * * * *